United States Patent [19]
Maurin et al.

[11] Patent Number: 5,744,154
[45] Date of Patent: Apr. 28, 1998

[54] READY-TO-USE INDOMETHACIN-BASED EYE LOTION

[75] Inventors: Florence Maurin, Vailhauques; Bernard Pages, Montbazin; Claude Coquelet, Saint Gely du Fesc, all of France

[73] Assignee: Laboratoire Chauvin S.A., Montpellier Cedex 1, France

[21] Appl. No.: 706,268

[22] Filed: Sep. 4, 1996

[51] Int. Cl.$^6$ .................... A61F 9/00; A61K 31/715
[52] U.S. Cl. ................ 424/427; 424/78.04; 424/78.05
[58] Field of Search ............. 424/427, 78.04, 424/78.05

[56] References Cited

U.S. PATENT DOCUMENTS

| | | | |
|---|---|---|---|
| 3,459,731 | 8/1969 | Gramera | 260/209 |
| 4,228,160 | 10/1980 | Szeftli et al. | 424/180 |
| 4,727,064 | 2/1988 | Pitha | 514/58 |
| 4,834,985 | 5/1989 | Elger et al. | 424/488 |
| 5,227,372 | 7/1993 | Folkman | 514/58 |
| 5,231,089 | 7/1993 | Bodor | 514/58 |

FOREIGN PATENT DOCUMENTS

| | | |
|---|---|---|
| 0 119 737 | 9/1984 | European Pat. Off. . |
| 0 244 315 | 11/1987 | European Pat. Off. . |
| 0 579 435 | 1/1994 | European Pat. Off. . |

OTHER PUBLICATIONS

Chemical Abstracts, vol. 98, No. 26, 6/27/83, Columbus, Ohio abstract No. 221812, XP002002860 & JP-A-57 200 361 (Sumitomo Chemical Co. Ltd., JP) 12/8/82.

*Primary Examiner*—Thurman K. Page
*Assistant Examiner*—Pamela S. Webber
*Attorney, Agent, or Firm*—Jacobson, Price, Holman & Stern, PLLC

[57] ABSTRACT

The present invention relates to a ready-to-use indomethacin eye lotion comprising, in aqueous solution:

indomethacin, a β- or γ-cyclodextrin etherified with $C_1$–$C_4$ alkyl or $C_1$–$C_4$ hydroxyalkyl groups, the cyclodextrin being present in a molar ratio with respect to the indomethacin of at least 10/1, and the pH of the solution being from 4.0 to 6.0.

6 Claims, No Drawings

READY-TO-USE INDOMETHACIN-BASED EYE LOTION

The present invention relates to a ready-to-use indomethacin-based eye lotion.

It is known that indomethacin is a product which is substantially insoluble in water and that it is hydrolysed in the presence of water in alkaline medium.

The use of various surfactants to dissolve indomethacin has already been recommended but the stability of the solutions obtained is not sufficient (Suleiman et al., Drug Development and Industrial Pharmacy, 16, 695, 1990) to make possible the manufacture of ready-to-use eye lotions.

To resolve these difficulties, the use has been proposed of lyophilized forms containing buffer mixture fractions which are redissolved in water containing the remainder of the buffer mixtures at the time of use (Patent FR 2,598,081).

Aqueous compositions containing indomethacin and a cyclodextrin have also been described.

Thus, EP-A-0 119 737 describes a hydrogel comprising indomethacin and β-cyclodextrin substantially in a 1/1 molar ratio, as well as L-arginine, and JP-A-57 200 361 describes a composition of the same type with a β-cyclodextrin/indomethacin molar ratio of approximately 2/1.

Moreover, in order to dissolve active principles which are unstable or which have little solubility in water, the formation of inclusion complexes with etherified β-cyclodextrins has been proposed (WO 85/02767), in particular at pH values in the region of 7.

The etherified β-cyclodextrins are used in an active principle/cyclodextrin molar ratio of 4/1 to 1/6.

It has now been discovered that it is possible to dissolve indomethacin in water and to obtain stable solutions using high proportions of etherified β- or γ-cyclodextrins and by using pH values from 4 to 6. Without wishing to limit the invention, it may be thought that, with high concentrations of etherified β- or γ-cyclodextrins, a complex is not formed but the indomethacin molecules are surrounded by a number of etherified β- or γ-cyclodextrin nuclei.

The present invention relates consequently to a ready-to-use indomethacin eye lotion comprising, in aqueous solution indomethacin β- or γ-cyclodextrin etherified with $C_1$–$C_4$ alkyl or $C_1$–$C_4$ hydroxyalkyl groups, the said cyclodextrin being present in a molar ratio with respect to the indomethacin of at least 10/1, and the pH of the solution being from 4.0 to 6.0.

Etherified β- and γ-cyclodextrins are compounds which are widely known and sold. They have cyclic structures composed respectively of 7 or 8 anhydroglucose units. Each of the glucose units contains 3 hydroxyl groups which are partially etherified with $C_1$–$C_4$ alkyl or $C_1$–$C_4$ hydroxyalkyl groups. The degree of substitution per anhydroglucose unit generally varies from 0.05 to 2, in particular from 0.2 to 2.

In the present invention, preference is very particularly given to hydroxypropyl-β-cyclodextrin but it is also possible to use in particular hydroxyethyl-β-cyclodextrin, hydroxybutyl-β-cyclodextrin and hydroxypropyl-γ-cyclodextrin. To obtain the best stability, preference is given to the use of etherified β- and γ-cyclodextrins, and very particularly hydroxypropyl-β-cyclodextrin, in a molar ratio of at least 25 with respect to the indomethacin.

The pH is preferably adjusted to between 4.5 and 5.5.

To prepare the eye lotions according to the invention, it is possible in particular to dissolve the indomethacin in the presence of the etherified β- or γ-cyclodextrin in an aqueous solution of an alkaline agent and then to adjust the pH to a value of 4 to 6 by addition of an acidic agent.

Use may be made, as alkaline agent for preparing the alkaline solution, of, in particular, arginine, sodium borate, sodium citrate or sodium acetate.

Use may be made, as acidic agent, of, in particular, hydrochloric acid, phosphoric acid, boric acid, glutamic acid, citric acid, acetic acid or sodium dihydrogenphosphate.

The eye lotion according to the invention can in addition contain an antimicrobial preservative, such as a mercurial derivative, a derivative of quaternary ammonium type or chlorhexidine.

The following examples illustrate the present invention.

EXAMPLE 1

The composition with the formula given in the table below is prepared by dissolving the indomethacin and hydroxypropyl-β-cyclodextrin (having a mean degree of substitution by hydroxypropyl groups of 0.4) in an aqueous arginine solution and by then adjusting the pH with the acid:

| COMPOSITION | |
|---|---|
| Indomethacin | 0.100 g |
| Hydroxypropyl-β-cyclodextrin | 10.00 g |
| Arginine | 0.120 g |
| Concentrated hydrochloric acid in the form of an N solution | q.s. pH 5.0 |
| Purified water, q.s. for | 100.000 ml |

The HPβCD/indomethacin molar ratio is approximately 27.5.

Under these conditions, complete dissolution of the indomethacin is obtained at 25° C. and the solution is stable for several months.

EXAMPLE 2

The procedure is as in Example 1, the following constituents being used:

Indomethacin 0.1 g

Hydroxypropyl-γ-cyclodextrin (having a mean degree of substitution of 0.6) 20.0 g Arginine and 1N hydrochloric acid, q.s. for pH=5.0

Distilled water, q.s. for 100.00 ml

Comparative Example 1

The procedure is as in Example 1, but using the following composition.

Indomethacin 0.1 g

β-Cyclodextrin 0.5 g

Arginine/Hydrochloric acid q.s. pH=5.0

Distilled water q.s. for 100.0 ml

Recrystallization is observed during manufacture, that is to say that it is not possible to obtain a 0.1% (w/v) indomethacin solution.

Tests on the Stability of the Eye Lotions According to the Invention

1. Stability after autoclaving:

Compositions are prepared as in Example 1, with different concentrations of hydroxypropyl-β-cyclodextrins.

Indomethacin 0.1 g

HPβCD (degree of substitution 0.4) from 5 to 30 g

Arginine/Hydrochloric acid q.s. pH=5.0
Purified water q.s. for 100.0 ml

The stability is studied after autoclaving for 20 minutes at 120° C. The results are given in the following table:

| HPβCD concentrations (g/100 ml) | | | | |
|---|---|---|---|---|
| 5 | 10 | 15 | 20 | 30 |
| 97.5% | 100% | 100% | 100% | 100% |

This table demonstrates the excellent stability of the compositions, especially for concentrations from 10 g of hydroxypropyl-β-cyclodextrin per 0.1 g of indomethacin, i.e. a molar ratio of approximately 27.5 with respect to the indomethacin.

2. Long-term stability at 25° and 40° C.

a) The stability of the following composition was tested:
Indomethacin 0.1 g
HPβCD (degree of substitution 0.4) 10.0 g
Arginine/Hydrochloric acid q.s. pH=5.0
Purified water q.s. for 100.0 ml The results are given in the table below:

| | Storage temperature | |
|---|---|---|
| T = (months) | 25° C. | 40° C. |
| 3 | 99.6% | 97.6% |
| 6 | 99.0% | 94.0% | b) The stability of the composition of Example 2 was tested. The results are as follows after 2 months.

| Storage temperature | Indomethacin level |
|---|---|
| 25° C. | 95% |
| 40° C. | 94% |

Comparative stability tests at pH 7

Compositions having the following formula were prepared:

Indomethacin 0.1 g
Hydroxypropyl-β-cyclodextrin (degree of substitution of 0.4) 0.5 to 50 g
Sodium borate/boric acid q.s. pH 7
Purified water q.s. for 100.0 ml The stability results at 40° C. are as follows:

| T (months) | Hydroxypropyl-β-cyclodextrin concentration | | | | |
|---|---|---|---|---|---|
| | 0.5 g | 2.5 g | 5 g | 20 g | 50 g |
| 1 | 81.3% | 89.7% | 90.7% | 92.7% | 93.0% |
| 2 | 70.7% | 82.5% | 85.0% | 85.0% | 87.0% |

These results show that the hydroxypropyl-β-cyclodextrin does not make it possible to obtain a satisfactory stability, even at relatively high concentrations, for solutions at pH 7.

We claim:

1. Ready-to-use indomethacin eye lotion comprising indomethacin and a beta- or gamma- cyclodextrin etherified with $C_1$–$C_4$ alkyl or $C_1$–$C_4$ hydroxyalkyl groups, in aqueous solution, wherein the cyclodextrin is present in a molar ratio of at least 10/1, with respect to indomethacin and the pH of the solution is from 4.0 to 6.0.

2. Eye lotion according to claim 1, in which the cyclodextrin is present in a molar ratio of at least 25 with respect to the indomethacin.

3. Eye lotion according to claim 1, in which cyclodextrin is hydroxypropyl-β-cyclodextrin.

4. Eye lotion according to claim 2, in which the cyclodextrin is hydroxypropyl-β-cyclodextrin.

5. Eye lotion according to claim 3, in which the hydroxypropyl-β-cyclodextrin has a degree of substitution by hydroxypropyl groups of 0.4.

6. Eye lotion according to claim 1, in which the pH is from 4.5 to 5.5.

* * * * *

UNITED STATES PATENT AND TRADEMARK OFFICE
CERTIFICATE OF CORRECTION

PATENT NO. : 5,744,154
DATED : April 28, 1998
INVENTOR(S) : Florence MAURIN, Bernard PAGES, and Claude COQUELET It is certified that error appears in the above-identified patent and that said Letters Patent is hereby corrected as shown below:

On the cover page of the patent, insert the following:

--[30]     Foreign Application Priority Data
     Sep. 6, 1995  [FR]  France....................95 10450--.

Signed and Sealed this

Third Day of November, 1998

Attest:

BRUCE LEHMAN

Attesting Officer

Commissioner of Patents and Trademarks